(12) United States Patent
Gulati

(10) Patent No.: US 11,920,105 B2
(45) Date of Patent: Mar. 5, 2024

(54) PROCESS FOR PRODUCING SYNTHETIC ABSOLUTES AND PRODUCTS THEREOF

(71) Applicant: BMV Fragrances [P] Ltd., Greater Noida (IN)

(72) Inventor: Mohit Gulati, Greater Noida (IN)

(73) Assignee: BMV Fragrances [P] Ltd., Greater Noida (IN)

( * ) Notice: Subject to any disclaimer, the term of this patent is extended or adjusted under 35 U.S.C. 154(b) by 280 days.

(21) Appl. No.: 17/425,295

(22) PCT Filed: Jan. 21, 2020

(86) PCT No.: PCT/IN2020/050065
§ 371 (c)(1),
(2) Date: Jul. 22, 2021

(87) PCT Pub. No.: WO2020/152704
PCT Pub. Date: Jul. 30, 2020

(65) Prior Publication Data
US 2022/0089970 A1     Mar. 24, 2022

(30) Foreign Application Priority Data
Jan. 22, 2019   (IN) .............................. 201911002598

(51) Int. Cl.
*C11B 9/02*     (2006.01)
*A61K 8/92*     (2006.01)
(Continued)

(52) U.S. Cl.
CPC .............. *C11B 9/025* (2013.01); *A61K 8/922* (2013.01); *A61Q 13/00* (2013.01); *B01D 11/0292* (2013.01); *B01D 11/0492* (2013.01)

(58) Field of Classification Search
CPC ..................................................... C11B 9/025
See application file for complete search history.

(56) References Cited

U.S. PATENT DOCUMENTS

| 9,340,751 | B2 | 5/2016 | Hölscher et al. |
| 2006/0003036 | A1 | 1/2006 | Shaath et al. |
| 2018/0230076 | A1 | 8/2018 | Thrun et al. |
| 2018/0305638 | A1* | 10/2018 | Bruening ................ C11B 9/025 |

FOREIGN PATENT DOCUMENTS

CN        105903227 A        8/2016

OTHER PUBLICATIONS

English Machine Translation CN105903227 obtained at Espacenet—Bibliographic data on Oct. 17, 2023 (Year: 2016).*
(Continued)

*Primary Examiner* — Arrie L Reuther
(74) *Attorney, Agent, or Firm* — Fulwider Patton LLP

(57) ABSTRACT

The present invention relates to the field of perfumery, that is, the art or process of making a fragrant substance be it natural or synthetic.

The present invention discloses a method of obtaining a better reconstituted absolute NNA+ (Near Natural Absolute) comprising the steps of:
a) mixing a synthetic absolute or raw reconstituted absolute with an alcohol;
b) freezing the solution of step (a);
c) filtering the solution of step (b) through a propylene cloth to separate out non-alcohol soluble substance and to obtain a crystal clear percolate;
d) transferring the percolate obtained from step (c) to an alcohol extraction unit, where said solution is boiled in a glass vessel at high temperature and vacuum to separate the alcohol;
e) allowing the solution of step (d) to stand for maturation of the reconstituted absolute NNA+.

10 Claims, 2 Drawing Sheets

(51) Int. Cl.
  *A61Q 13/00* (2006.01)
  *B01D 11/02* (2006.01)
  *B01D 11/04* (2006.01)

(56) References Cited

OTHER PUBLICATIONS

International Search Report, 4 pages, dated Jun. 8, 2020.
Written Opinion of the International Search Authority, 6 pages, dated Jun. 8, 2020.
Supplementary European Search Report for European Patent Application No. 20 74 6026.2, dated Nov. 18, 2022 (3 pages).
European Search Opinion for EP 20 746 026.2, dated Nov. 18, 2022 (7 pages).
Examination Report for India Patent Application No. 201911002598, dated May 23, 2023 (6 pages).
Galikhanov, M.F., "Unipolar Corona Discharge Effect on Filtering Capacity of Polypropylene Non-Woven Fabrics," Fibre Chemistry, vol. 48, No. 6, Mar. 2017, pp. 473-477.
Handa, Sukhdev Swami, et al., "Extraction Technologies for Medicinal and Aromatic Plants," United Nations Industrial Development Organization and the International Centre for Science and High Technology, 2008 (266 pages).
"Fragrance Extraction," from Wikipedia, https://web.archive.org/web/20130522203433/https://en.wikipedia.org/wiki/Fragrance_extraction, (3 pages).
"Extraction Methods," from Eden Botanicals, https://web.archive.org/web/20161116025209/https://www.edenbotanicals.com/extraction-methods (3 pages).

* cited by examiner

PROCESS FOR PRODUCING SYNTHETIC ABSOLUTES AND PRODUCTS THEREOF

CROSS-REFERENCE TO RELATED APPLICATIONS

This application is the U.S. National Stage of International Application No. PCT/IN2020/050065, filed Jan. 21, 2020, which claims priority to Indian Patent Application No. 201911002598, filed Jan. 22, 2019.

FIELD OF INVENTION

The present invention relates to the field of perfumery, that is, the art or process of making a fragrant substance be it natural or synthetic.

BACKGROUND OF INVENTION

Perfume (French: parfum) is a mixture of fragrant essential oils or aroma compounds, fixatives and solvents, used to give the human body, animals, food, objects, and living-spaces an agreeable scent. It is usually in liquid form and used to give a pleasant scent to a person's body. Ancient texts and archaeological excavations show the use of perfumes in some of the earliest human civilizations. Modern perfumery began in the late 19th century with the commercial synthesis of aroma compounds such as vanillin or coumarine, which allowed for the composition of perfumes with smells previously unattainable solely from natural aromatics alone.

In today's world of perfumery, the perfumers face a huge problem of procuring the natural essential oils from around the world. With so much civilization and cutting off of the natural habitats around the world, there is a shortage in the availability of the natural product. This also leads to the farmers or the producers following different practices to make up for the ever-growing supply. This in turn leads to variations to the product, which is a precarious situation for the perfumers.

This led to usage of synthetic reconstitutions of natural products in perfumery and flavours as well. reconstitution literally means building up again. a reconstitution is an attempt by the creator that it is olfactorily and somewhat visually similar to the natural counterpart so much so that it can replace the pure product. this reconstitution is generally cheaper in price. the biggest advantage of these reconstitutions is the stability of the product, that is, if the reconstitution will not have variations since it is a formula just like any other fragrance.

As per the book by Stefan Arctander, as absolute in a prepared perfumery material. Absolutes are highly concentrated, entirely alcohol soluble and usually liquid perfumery material. They are obtained by alcohol extraction of concretes or resinoids. Usually the alcohol soluble fraction of a resinoid is called an Absolute.

OBJECT OF INVENTION

The main object of the invention is abating a synthetic absolute through aromatic chemicals, natural aromatic products or other reconstituted oils and absolutes to obtain a product that is organoleptically similar to the natural product.

It is an object of embodiments described herein to address the limitations and problems faced to counter the demand of natural absolutes and also substituting it with reconstituted absolutes.

It is another object of the invention is obtaining an alcohol soluble and a better synthetic absolute. A method performed by the alcohol soluble extraction for the evaluation of a synthetic absolute named NNA+ (Near Natural Absolutes)

BRIEF DESCRIPTION OF INVENTION

The perfumer achieves this build-up of the reconstitution by mainly two tools, namely, a GCMS-Gas Chromatography-Mass Spectrometry and a perfumer' organoleptic senses. Firstly, a GCMS, is an analytical method that combines the features of Gas Chromatography and mass spectrometry. This method identifies the different substances within a test sample. The perfumer analyses and studies analytical report created by the GCMS. An example of the GCMS report is identified compounds from the agar oil extracted from fungal infected Agarwood by GCMS S. 1. Cyclopentadecanol 7.421% 2. Decanoic acid 8.839% 3. 4-(4-methoxyphenyl)-2-butanone 8.914% 4. Pentadecanoic acid 9.139% 5. 3-methyl-2-(2-methyl-2-butenyl)-furan 10.190% 6. Pentadecanoic acid-15 Bromo 10.715% 7. 2-isobutyl-3methyl furan 10.940% 8. Oleic acid 11.107% 9. 3-methyl-2-(2-oxopropyl) furan 11.307% 10. Tetradecanoic acid 11.723% 11. Hexadecanoic acid, 14 methyl, methyl ester 13.675% 12. Heptatriactontadien-2-one 13.501% 13. 4-hydroxy-3,5-dimethoxybenzyldehyde 13.767% 14. 4 phenyl-2-butatone 11.857% 15. (S)-4a-methyl-2-(1-methylethyl)-3,4,9,5,6,7-hexahydro-naphthalene 12.808% 16. 4-hydroxy-3,5-dimethoxybenzyldehyde 15.360% 17. Bis (2-ethylhexyl) phthalate 15.410%

This report helps the perfumer to build the base of his reconstitutions by identifying the main components of the natural absolute and substituting them with similarly smelling compounds. For examples one of the products is built up as shown in table 1.

Secondly, the organoleptic properties, the perfumer applies his/her knowledge, experience and the organoleptic senses to cement the edges of the base created. He does this by adding essential oils, absolutes, synthetic essential oils, absolutes to recreate the smell or flavour of the natural counterpart.

After many experiments, the final product is obtained. This product is called a reconstitution. A product which smells almost or somewhat similar to the natural product.

But there is always a difference between the two products. This difference depends on two things. The talent, skill and its application of the perfumer., i.e. the analysis of the GCMS plus the understanding of the natural product organoleptically.

Secondly, the difference between nature and manmade product. A natural product can never be 100% duplicated. The reconstitution will always be a reconstitution. A natural absolute can never have a perfect substitute.

But as the modern perfumery is now the art of substitutes, BMV Fragrances Pvt. Ltd. experimented and tried to bridge this gap. The natural absolutes from the raw material are obtained by following two steps:

1. Hydrocarbon solvent extraction of the natural raw material/plant etc. The material obtained after this process is called either a resinoid or a concrete.

2. The next step is the alcohol extraction of the concrete or the resinoid obtained the previous step.

The 2nd step being of the utmost importance because of the physical property of the absolute to be alcohol soluble.

BMV Fragrances Pvt. Ltd. applied this practice on synthetic or reconstituted absolutes by considering the reconstitutions as resinoids and performing alcohol extraction on them to obtain a better reconstitution.

EXPERIMENTAL METHOD

Figure 1:
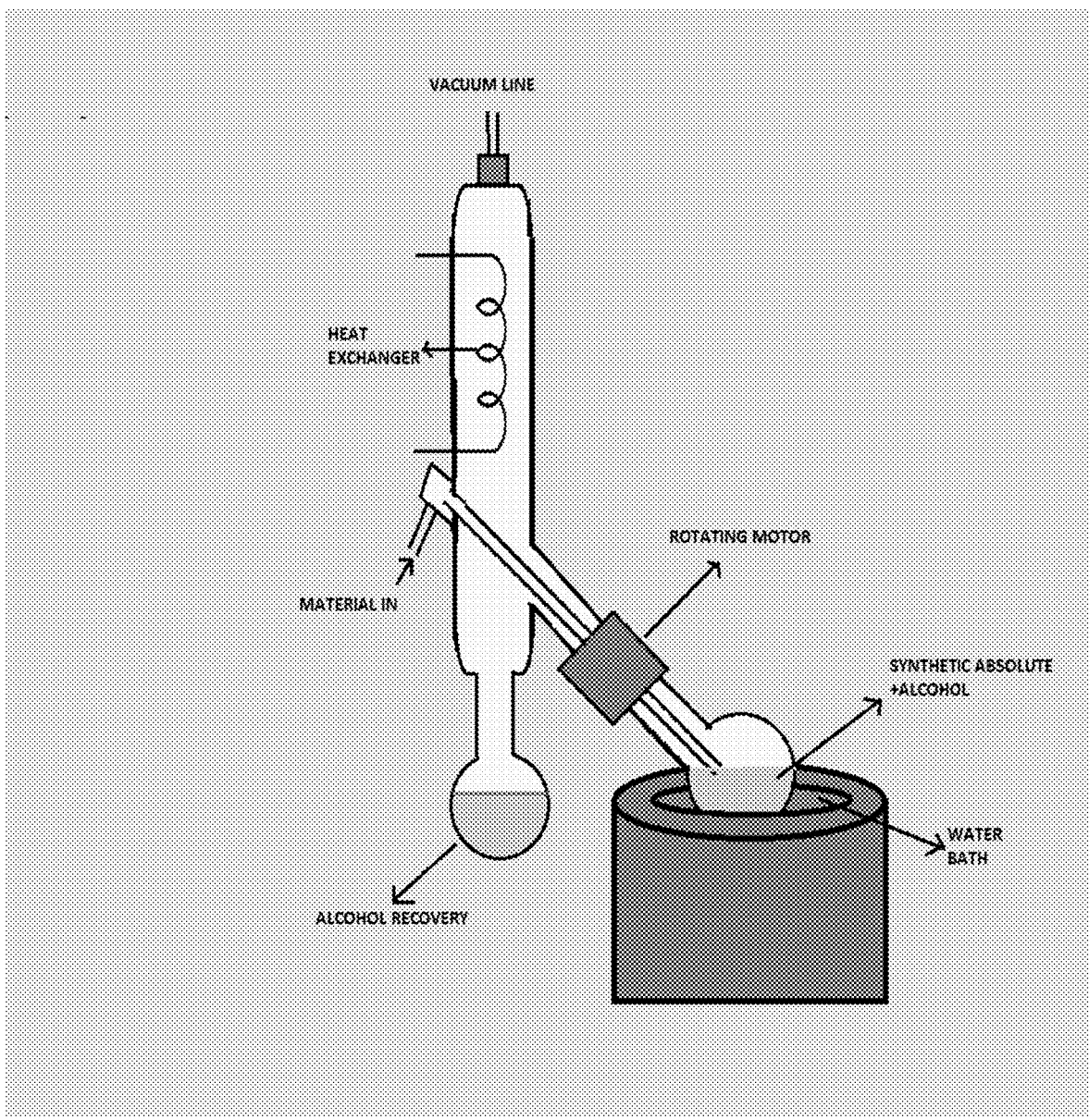
FIG. 1: Shows the diagrams for the experimental set up for the alcoholic extraction of the reconstituted absolute.
Figure 2:
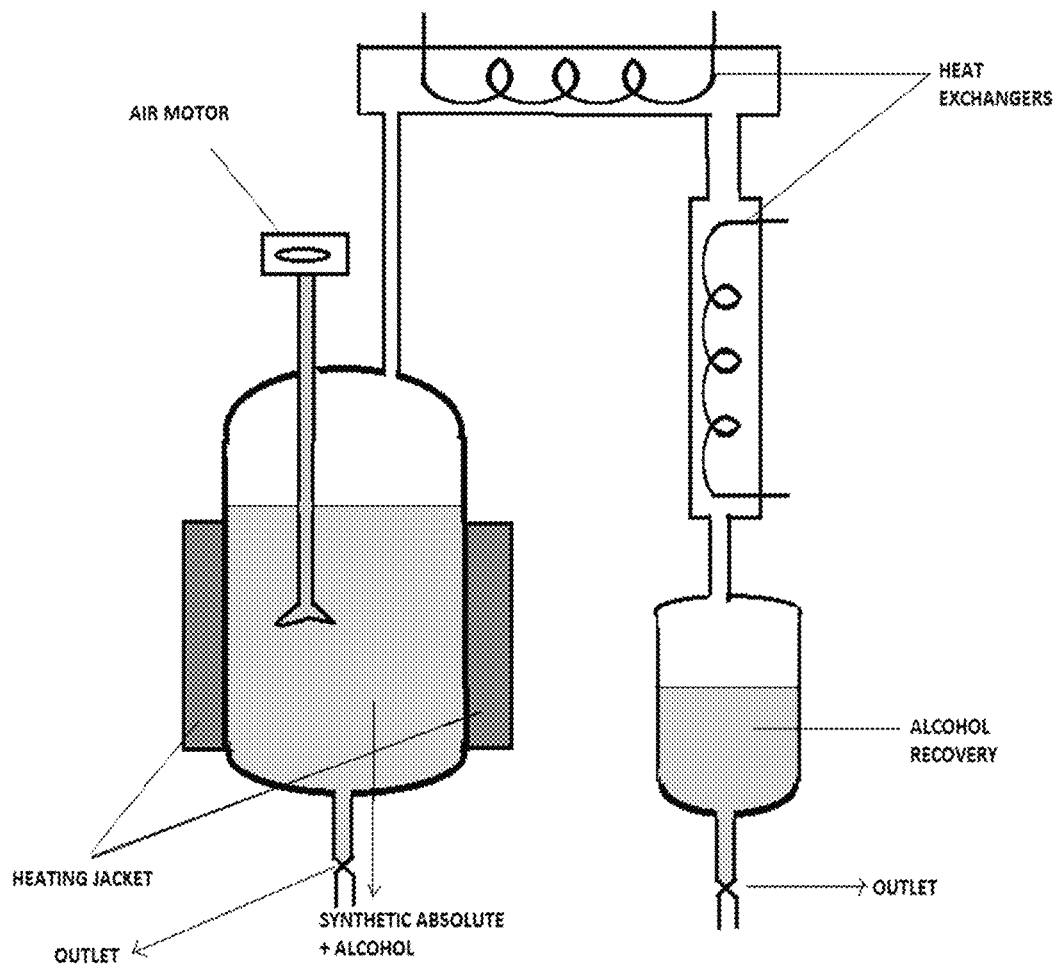
FIG. 2: The commercial set up.

For this method, a synthetic compound aimed to be reconstituted absolute is required. An alcohol extraction unit is required to extract the alcohol.

1st step, the synthetic compound is mixed with 99% alcohol. This is generally done at a ratio depending on the viscosity and the density of the compound. The minimum ratio being 1 part compound and 3 parts alcohol whereas the maximum is 1 part compound and 10 arts of alcohol.

This will provide us with a solution partly or purely soluble in alcohol.

To test any deposition of the solution, this solution is kept at a temperature of −20 degree Celsius for about 30 minutes. The duration again depends on the quantity of the solution. If the quantity is more, the duration is more.

The above step is taken to allow the alcohol to extract all the alcohol soluble substances from the compound.

After freezing the solution for a duration of time under −20 degree Celsius, the obtained solution is either soluble or partially soluble. To sieve out all the non soluble matter, the solution is made to go through a polypropylene cloth.

All the non soluble matter is not required. This is usually less than 10% of the compound. The cloth strains all the non soluble matter. This loss of material is one of the losses in this method, a necessary one.

After sieving the solution, we obtain an alcohol soluble substance, crystal clear percolate, which is still with alcohol mixed in it that is the required NNA+ product along with alcohol.

We need to separate this alcohol to obtain the desired product. This done by transferring the solution in an alcohol extraction unit.

This alcohol extraction unit boils this solution in a glass vessel under controlled heat and vacuum. Water is usually the best approach to provide the heat.

Alcohol, being a solvent, with a low boiling point of 78 degree Celsius, this boiling point reduces in a solution. The alcohol usually begins to evaporate at a temperature around 60 degrees. The temperature increases to 80 degrees and now water along with alcohol is separated out. Till the temperature is increased to about 110 degree Celsius, all the water is extracted and the required material is left. To increase the rate of the process vacuum is required sometimes.

The material in the glass vessel is the required alcohol soluble reconstituted absolute called NNA+. The GCMS analysis report is shown in Table 2.

This NNA+ is made to stand and settle for 48 to 72 hours to mature. After the NNA+ is mature then it is transferred for evaluation.

The evaluation shows that the NNA+ is better than the original compound organoleptically.

Evaluation Example

Oudh Makkaj NNA

Organoleptic Properties:

Colour/Appearance: Dark brown viscous liquid.

Odour: Sharp woody, Sweet balsamic, somewhat harsh.

Taste: Bitter taste.

Solubility: Not entirely soluble in Alcohol

Oudh Makkaj NNA+

Organoleptic Properties:

Colour/Appearance: Dark brown clear viscous liquid.

Odour: Woody balsamic sweet rich odour of Agarwood.

Solubility: Soluble in alcohol

Taste: Bitter taste.

Commercial Method

Similarly to the experimental method, the commercial method starts with the raw reconstituted absolute. The quantity is more than the experiment sample. Let us say the quantity is a 25 kilo grams.

The alcohol is used in this method is Iso Propyl Alcohol. The reasons behind using Iso Propyl Alcohol are that this alcohol is commercially viable, feasible and safer than pure ethyl alcohol.

The method is as follows:

First, we mix the reconstituted absolute with Iso Propyl Alcohol at a ratio of 1:3. The ratio depends on the viscosity and the quantity of the raw material.

Secondly, this solution is allowed to rest under −20 degree Celsius for no less than 1 hour.

After decantation of the non soluble matter, this material is put through a sieve. After sieving, the non alcohol soluble matter is separated.

The solution is transferred to an alcohol extraction unit where this solution is kept at a high temperature and vacuum to extract the alcohol.

After 3 to 4 hours of extraction, this solution is allowed to stand for 48 to 72 hours to mature.

After maturity, the commercial NNA+ is ready to be shipped.

Losses

Loss of insoluble matter.

Because of the physical property of an absolute to be alcohol soluble, the non alcohol soluble matter is removed through freezing and sieving. This improved the odour profile of the final product as well. This purely depends on the composition of the reconstituted raw absolute and this is generally constant regardless of the quantity of a specific material.

Handling Losses

Transferring of material from one unit to another unit or tank leaves a handling loss. The percentage of handling loss is less for higher quantities.

Tables and Diagrams

TABLE 1

| S. No. | Oudh Makkaj NNA | Percentage |
| --- | --- | --- |
| 1 | Alpha Pinene | 0.11 |
| 2 | Beeta Pinene | 0.24 |
| 3 | Benzyl Acetone | 6.53 |
| 4 | Alpha Copaene | 0.52 |
| 5 | Cyperene | 1.18 |
| 6 | Alpha Gurjunene | 24.58 |
| 7 | Alpha Santalene | 1.72 |
| 8 | Calarene | 5.01 |
| 9 | Allo Aromadendrene | 6.76 |
| 10 | Longipinene | 4.76 |
| 11 | Zingiberene | 0.76 |
| 12 | Valencene | 0.95 |
| 13 | Beta Bisabolene | 2.24 |
| 14 | Beta Himachelene | 0.24 |
| 15 | Elemol | 2.79 |

TABLE 1-continued

| S. No. | Oudh Makkaj NNA | Percentage |
|---|---|---|
| 16 | Delta Gurjunene | 2.86 |
| 17 | Gaama Eudesmol | 2.24 |
| 18 | Valerianol | 11.6 |
| 19 | Eicosane | 3.34 |

TABLE 2

| S. No. | Oudh Makkaj NNA+ | Percentage |
|---|---|---|
| 1 | Alpha Pinene | 0 |
| 2 | Beeta Pinene | 0.04 |
| 3 | Benzyl Acetone | 6.14 |
| 4 | Alpha Copaene | 0.48 |
| 5 | Cyperene | 1.13 |
| 6 | Alpha Gurjunene | 22.2 |
| 7 | Alpha Santalene | 0 |
| 8 | Calarene | 4.4 |
| 9 | Allo Aromadendrene | 6.78 |
| 10 | Longipinene | 4.43 |
| 11 | Zingiberene | 0.8 |
| 12 | Valencene | 0.95 |
| 13 | Beta Bisabolene | 2.48 |
| 14 | Beta Himachelene | 0 |
| 15 | Elemol | 3.2 |
| 16 | Delta Gurjunene | 0 |
| 17 | Gaama Eudesmol | 2.76 |
| 18 | Valerianol | 10.76 |
| 19 | Eicosane | 3.09 |

I claim:

1. A method of obtaining a reconstituted absolute NNA (Near Natural Absolute) comprising the steps of:
   a) mixing a synthetic absolute or raw reconstituted absolute with an alcohol;
   b) freezing the solution of step (a);
   c) filtering the solution of step (b) through a propylene cloth to separate out non-alcohol soluble substance and to obtain a clear percolate;
   d) transferring the percolate obtained from step (c) to an alcohol extraction unit, where said solution is boiled in a glass vessel at boiling temperature and vacuum to separate the alcohol;
   e) allowing the solution of step (d) to stand for maturation of the reconstituted absolute NNA.

2. The method as claimed in claim 1, wherein the ratio of the synthetic absolute or raw reconstituted absolute with an alcohol is about 1:3.

3. The method as claimed in claim 1, wherein the ratio of the synthetic absolute or raw reconstituted absolute with an alcohol is at most 1:10.

4. The method as claimed in claim 1, wherein the alcohol used for mixing the synthetic absolute or raw reconstituted absolute is isopropyl alcohol.

5. The method as claimed in claim 1, wherein the freezing of solution in step (b) is carried at −20° C.

6. The method as claimed in claim 1, wherein the freezing of solution in step (b) is carried for at least 30 minutes.

7. The method as claimed in claim 1, wherein the propylene cloth is 500 mesh cloth.

8. The method as claimed in claim 1, wherein a boiler is used to provide the heat for boiling the solution in the alcohol extraction unit.

9. The method as claimed in claim 1, wherein the solution in step (e) is allowed to stand for 48 to 72 hours.

10. The method as claimed in claim 1, wherein the reconstituted absolute NNA has organoleptic properties.

* * * * *